US006689740B1

(12) United States Patent
McGee et al.

(10) Patent No.: US 6,689,740 B1
(45) Date of Patent: Feb. 10, 2004

(54) METHOD FOR PREPARING FRAGRANCE PRODUCTS

(75) Inventors: Thomas McGee, Nesles la Vallee (FR); Kenneth Leo Purzycki, Lake Parsippany, NJ (US); Richard P. Sgaramella, Hoboken, NJ (US)

(73) Assignee: Givaudan SA, Vernier (CH)

( * ) Notice: Subject to any disclaimer, the term of this patent is extended or adjusted under 35 U.S.C. 154(b) by 191 days.

(21) Appl. No.: 09/583,587

(22) Filed: May 31, 2000

Related U.S. Application Data

(60) Provisional application No. 60/139,278, filed on Jun. 15, 1999.

(51) Int. Cl.[7] .................................................. A61K 7/46

(52) U.S. Cl. ............................... 512/2; 512/1; 510/515; 510/519; 510/520

(58) Field of Search ......................... 512/1, 2; 510/515, 510/519, 520

(56) References Cited

U.S. PATENT DOCUMENTS 3,650,816 A * 3/1972 Rudy et al. ................... 427/11
3,686,025 A 8/1972 Morton
3,989,631 A * 11/1976 Marsan ....................... 510/515
4,014,105 A 3/1977 Furgal et al.
4,073,996 A 2/1978 Bedenk et al.
4,209,417 A 6/1980 Whyte
4,537,877 A 8/1985 Ericsson
4,954,285 A 9/1990 Wierenga et al.
4,983,422 A 1/1991 Davis et al.
5,246,603 A * 9/1993 Tsaur et al. ................. 510/519
5,286,400 A 2/1994 Paszek et al.
5,348,667 A 9/1994 Bacon et al.
5,656,584 A 8/1997 Angell et al.
5,763,083 A 6/1998 Berrigan
5,783,543 A 7/1998 Fleckenstein et al.
6,297,210 B1 * 10/2001 Hsu et al. ................... 510/520

FOREIGN PATENT DOCUMENTS

CH 541 655 10/1973
EP 0 536 942 A2 4/1993
EP 816 484 1/1998

* cited by examiner

*Primary Examiner*—Jill Warden
*Assistant Examiner*—Monique T. Cole
(74) *Attorney, Agent, or Firm*—Norris McLaughlin & Marcus

(57) ABSTRACT

The present invention relates to a process for reducing fragrance loss in a substrate. This process includes preparing a protected fragrance matrix that contains a perfume, an optional fixative and a solid absorbent. The process further includes combining a substrate conditioner with the fragrance matrix and a substrate. Products, especially fabric softener sheets, made from these processes are also provided.

25 Claims, No Drawings

METHOD FOR PREPARING FRAGRANCE PRODUCTS

This application claims the benefit of Provisional Application Ser. No. 60/139,278 filed Jun. 15, 1999.

FIELD OF THE INVENTION

The present invention relates to substrates having prolonged fragrance. More particularly, the present invention provides compositions and methods for reducing the loss of perfume during manufacture.

BACKGROUND OF THE INVENTION

Fabric softener sheets typically include a substrate, a fabric conditioner base and a fragrance. The fabric conditioner base is used to impart a benefit to a fabric treated therewith. Such a benefit may include, for example, softness, reduced static of dried articles, easier ironing, etc. The fragrance is a used to impart a pleasant aroma to the dried fabric.

In use, these fabric softener sheets are typically placed in a conventional dryer together with fabric to be dried, e.g., wet laundry. During the drying process, fragrance and other benefits are transferred from the fabric softener sheet to the fabric being dried.

Conventionally, a fabric softener sheet is manufactured by coating a mixture of fabric conditioner base and fragrance onto a substrate. Typically, fabric softener bases are solid mixtures that must be melted prior to use. In practice, fabric conditioner bases are melted in a holding tank at about 70° C. to 90° C. then fragrance is added. Depending on the speed of coating, the conditioner base and fragrance may remain at these elevated temperatures for 4 to 8 hours. Fabric softener sheets are coated by continuously passing a substrate, e.g., a polyester sheet material, at high speed through a coating tank that is also held at 70° C. to 90° C. The coated sheet material is then passed through a series of cooled rollers and a cooling tower to reduce the sheet temperature to about 30° C.

Fragrance losses occur at various points during the conventional fabric sheet manufacturing process; these losses in total may be up to 30 percent to 45 percent.

Encapsulates, such as cyclodextrin compositions as outlined in Bacon, et al., U.S. Pat. No. 5,348,667, have been used to reduce perfume loss during the manufacturing process. Such encapsulation technology, however, is expensive to make and use, and is therefore not cost effective in a large-scale commercial setting.

Absorbents have been used to carry lipophilic materials such as fragrance in the manufacture of certain products. For example, it is known that solids can adsorb oily materials, such as, perfume. Such adsorbent solids have been reportedly used as carpet cleaning powders (U.S. Pat. No. 5,783,543 and U.S. Pat. No. 5,286,400), in oil adsorbent products (U.S. Pat. No. 4,537,877 and U.S. Pat. No. 5,763,083), in detergent powders (U.S. Pat. No. 5,656,584), in detergent liquids (U.S. Pat. No. 4,983,422 and U.S. Pat. No. 4,209,417), in detergent bars (EP 816484), and in liquid softeners (U.S. Pat. No. 4,954,285).

Accordingly, one object of the present invention is to provide a process for producing a fabric softener sheet which process significantly reduces the loss of the perfume in the fragrance matrix during the manufacture of such a sheet compared to conventional processes.

Another object of the invention is to provide a substrate having prolonged fragrance compared to conventionally prepared substrates.

Another object of the invention is to provide an efficient, cost-effective method for reducing the loss of perfume during the manufacture of fabric softener sheets.

The present invention is directed to meeting these and other objects.

SUMMARY OF THE INVENTION

The present invention provides a process for reducing fragrance loss during the manufacturing of fragranced substrates. This process includes providing a protected fragrance matrix that contains a perfume, a solid absorbent and optionally a fixative. In this process, a fabric conditioner base is further provided. A substrate is then combined with the fragrance matrix and the fabric conditioner base. A substrate treated in this manner retains more of the fragrance compared to conventionally prepared substrates.

The present invention also provides a substrate impregnated with a fragrance matrix having prolonged organoleptic activity. This substrate is made by the process of forming a protected fragrance matrix that includes a perfume, an optional fixative and a solid absorbent. The fragrance matrix is then combined with a fabric conditioner base. The fragrance matrix and fabric conditioner base are then applied to the substrate either together as a mixture or sequentially. In this process, the fragrance matrix is combined with the fabric conditioner base immediately prior to application of the mixture to the substrate. Alternatively, the fragrance matrix is applied to the substrate immediately after the fabric conditioner base.

DETAILED DESCRIPTION OF THE INVENTION

The present invention provides a low cost method of reducing the loss of perfume during the manufacture of, e.g., a fabric softener sheet. This process includes the addition of a protected, i.e., an enrobed perfume contained within a fragrance matrix to a fabric conditioner base prior to application of the fabric conditioner base onto or into a substrate or during one of the rolling stages of a conventional fabric softener sheet manufacturing process. By using the process of the present invention, it is easier to dose, i.e., apply the fragrance to the substrate during the manufacturing process when the perfume is in a solid carrier form.

Thus, the process of the present invention includes ( 1) preparing a fragrance matrix including an enrobed, i.e., a protected perfume, an optional fixative and a solid absorbent; and ( 2) combining the fragrance matrix with a fabric conditioner base and a substrate.

As used herein, the phrase, "fabric softener sheet" includes a substrate, a fabric softener base and a fragrance matrix. For purposes of the present invention, the term "substrate" is intended to mean any material that acts as a delivery vehicle for the fragrance matrix and fabric conditioner base. Thus, in the present invention, the substrate must be able to retain in its interior or on its surface a sufficient quantity of the fabric conditioner base and fragrance matrix required to deliver the desired performance (prolonged fragrance) to the fabric, e.g., a fabric softener sheet. Typically, the substrate is in the form of a sheet, although other forms may be used. The substrate may be a synthetic or natural fiber that is woven, knitted or extruded. Non-limiting examples of materials that may be used as a substrate in the present invention include cotton, Rayon, polyester, regenerated cellulose, and the like.

As used herein, the phrases "fragrance matrix" or "protected fragrance matrix" mean that at least the most volatile parts of a perfume are protected or enrobed by a solid absorbent and optionally a fixative to reduce the amount of loss of fragrance during the manufacturing process of a substrate through evaporation of the perfume volatiles.

In the present invention, the protected fragrance matrix is said to "enrobe" the perfume. Thus, as used herein, the terms "enrobe," "enrobed" or "enrobement" refer to the sequestration of the perfume in the protected fragrance matrix to reduce the loss of fragrance during the manufacture of fragranced substrates, e.g., fabric softener sheets, and to prolong the effect of a fragrance on substrates coated with such an enrobed perfume.

The protected fragrance matrix is preferably in the form of a flowable powder. Thus, the ratio of perfume, solid absorbents and fixative are carefully controlled to maintain the consistency of a flowable powder. In this embodiment, the perfume-to-solid absorbent ratio is between about 1:20 to about 2:5, preferably about 1:5. The level of perfume, however, will depend upon the final composition of the substrate. The fragrance, in turn, may be present in the protected fragrance matrix in an amount of from about 10% to about 50% (wt/wt), preferably, in an amount of from or between about 20% to about 40% (wt/wt). On the substrate, the fragrance level will be about 1% to about 6% (wt/wt).

The flowable powder may be dosed into, for example, a molten fabric conditioner base such as a softener or an antistatic system. Preferably, the powder is mixed into the fabric conditioner base immediately prior to application of the mixture to the substrate. Alternatively, the powder is applied to a substrate previously coated with the fabric conditioner base at a subsequent processing step, such as at one of the rolling stations during the manufacture of a fabric softener sheet.

As used herein, the term "immediately" is intended to mean that the fragrance matrix is added to the fabric conditioner base just prior to application to the substrate. Typically, the fragrance matrix is added 1–20 minutes prior to application to the substrate, preferably 2–10 minutes prior to application to the substrate; most preferably the fragrance matrix is dosed at the rolling stage directly onto the substrate coated with the fabric conditioner base.

In the present invention, the protected fragrance matrix may contain all or part of the perfume. If part of the perfume is protected, i.e., enrobed, then it is usual to select the most volatile components to be enrobed.

For example, in the present invention, the protected fragrance matrix is formed into a powder by mixing the perfume with an absorbent solid and an optional fixative. Absorbent solids that may be used in accordance with the present invention include, for example, clays, silicas, Celites, Zeolites, metal salts, including for example phosphates, cellulose, such as methyl cellulose, starches, carbonates, such as sodium bicarbonate, borates, such as sodium borate, sulfates, such as sodium sulfate, water-soluble polymers, Borax and mixtures thereof.

For purposes of the present invention, the term "perfume" is intended to mean a mixture of a single or complex mixture of aromatic chemicals which have been formulated to give an aesthetically pleasing smell to a substrate, such as for example, a fabric softener sheet. As used herein, "aroma chemicals" are intended to mean chemicals that have an odor. There are many chemical classes which fall within the meaning of the phrase "aroma chemicals" as used herein, including for example, hydrocarbons, alcohols, aldehydes, ketones, lactones, esters. These chemical classes are described in S. Arctander Perfume Flavors and Chemicals, Vols. 1 and 2, Arctander, N.J. USA which also is hereby incorporated-by-reference.

The perfume may also contain small amounts of other additives, such as solvents, preservatives, antioxidants, UV screening agents and the like. The fragrance matrix may also include organoleptic components, such as for example, other well-known fragrance ingredients.

Preferably, a fixative is incorporated into the fragrance matrix of the present invention. The fixative preferably is a high molecular weight, low melting solid composition that may be mixed into a powder. Examples of suitable fixatives for use in the present invention include polyethylene glycol, Glycerox, mineral oil and mixtures thereof. In accordance with the present invention, the molecular weight of the fixative may vary between about 400 to 20,000 daltons, preferably between about 2,000 to 10,000 daltons. Other fixatives having a similar viscosity and melting point to polyethylene glycol are also contemplated by the present invention. The level of fixative useful in accordance with the present invention is between about 1% and about 40% (wt).

The solids and the liquids set forth above are combined by, for example mixing in a suitable mixer until the blend is flowable so that it is easy to apply (i.e., dose) to a substrate.

The present invention also includes a fabric conditioner base. For purposes of the present invention, the fabric conditioner base includes a mixture of ingredients that impart a desired property to the fabric, such as for example, softness, no static cling, reduced creasing, easier ironing, and the like. These properties are achieved using, for example, cationic, zwitterionic, and non-ionic softeners, soaps and quaternary compounds, as well as other fatty materials alone or in combination. Other examples of suitable fabric softener bases may be found in U.S. Pat. No. 3,686,025, which is hereby incorporated by reference as if recited in full herein.

Other optional components may also be added to the fabric conditioner base to further impart various desired characteristics to the substrate, so long as these ingredients do not significantly interfere with the reduction of fragrance loss during manufacturing of substrates. Such optional components include, for example, antistatic agent(s), anti dye-transfer agent(s), soil release agent(s), and the like.

In the process according to the present invention, the substrate may be coated at several carefully timed points and according to a specific sequence of events to achieve the desired fragrance effect. For example, in one embodiment, the substrate may be coated by combining the fragrance matrix with the fabric conditioner base to form a mixture immediately prior to applying the mixture to the substrate. Alternatively, the substrate is coated by applying the fabric conditioner base thereto to form a substrate-fabric conditioner base composition. Thereafter, the fragrance matrix is applied to the coated substrate.

For purposes of the present invention, the fragrance matrix and/or fabric conditioner base is applied to the substrate using any conventional technique suited for the particular application, such as, for example, spraying, coating, dipping and the like. Using these and other techniques, the fragrance matrix and fabric conditioner base are applied to the substrate as a coating. Alternatively, the fragrance matrix and fabric conditioner are impregnated throughout the substrate, i.e., are dispersed within the interstitial matrix of the substrate as well as its surface.

Preferably, the fabric conditioner base and fragrance matrix are dispersed throughout the substrate to a uniform thickness of about 0.1 to about 2 mm to evenly distribute the fragrance throughout the entire substrate.

Another embodiment of the present invention is a substrate impregnated with a fragrance matrix having prolonged organoleptic activity. This substrate is made by the process which includes (a) forming a protected fragrance matrix as set forth previously with a perfume, a fixative and a solid absorbent; and (b) mixing the fragrance matrix with the fabric conditioner base immediately prior to applying the mixture to the substrate or applying the fragrance matrix to the substrate immediately after the fabric conditioner base is applied to the substrate.

Thus, in one embodiment, a mixture of the fragrance matrix and fabric conditioner base is applied to the substrate. In this embodiment, the fragrance matrix is added to the fabric conditioner immediately prior to application of the mixture to the substrate. Alternatively, the fabric conditioner base and fragrance matrix are applied to the substrate sequentially. In this embodiment, the fabric conditioner is applied to the substrate first, immediately followed by the fragrance matrix.

The fixative according to this embodiment is selected from high molecular weight, low melting point compositions such as for example, polyethylene glycol, Glycerox, mineral oil and mixtures thereof.

The following examples are set forth to illustrate the processes and compositions of the present invention. These examples are provided for purposes of illustration only and are not intended to be limiting in any sense.

EXAMPLES

Example 1

Enrobed Composition

An enrobed, i.e., protected fragrance matrix was made by combining the ingredients as set forth below:

| Component | % |
|---|---|
| Perfume Oil (Givaudan Roure) Fragrance PNF217FPN | 20 |
| Polyethylene Glycol 4000 (Union Carbide) | 1 |
| Bentonite H (Whitaker, Clark & Daniels) | 10 |
| Valfor 100 Aluminosilicate Zeolite (PQ Corp.) | 69 |

Example 2

Comparison of Fragrance Retention of Enrobed Composition vs. Control

A comparison between a fabric softener sheet made using a conventional process and a fabric softener sheet made according to the processes of the present invention are set forth below.

Control

A conventional fabric softener base, Varisoft 136-100 (Witco, Inc. OH) was heated to 80° C. in a convection oven. 48 grams of this composition was placed in a pre-heated beaker and 2 grams of the perfume oil PNF217FPN (fragrance level=4%) was added to the beaker with agitation. The mixture was held at 80° C. for 4 hours to simulate production and then applied to a commercially available polyester softener sheet in a pilot plant using a coating machine (Talbot Engineering Corp.).

Enrobed Composition

Varisoft 136-100 was heated to 80° C. and 40 grams thereof was placed in a pre-heated beaker as described above. 10 grams of the protected fragrance matrix ( 20% PNF217FPN=4% fragrance) according to Example 1 was added to the Varisoft with mixing immediately prior to application of the mixture onto a fabric softener sheet in a pilot plant.

On cooling, the fragrance level in the control and enrobed softener sheets was determined by extraction and analysis by gas chromatography/mass spectrometry. The results are shown below:

| Percent of theoretical fragrance level | |
|---|---|
| Control Sheet | 28.8 |
| Enrobed Sheet | 43.2 |

As the data above indicates, perfume loss in the pilot plant was reduced from 71% to 57% using the late addition of a protected fragrance matrix (Enrobed Sheet) compared to the control sheet.

Example 3

Enrobed vs. Unprotected Compositions in Open/Closed Systems

The manufacture of fabric softener sheets requires that a melted fabric softener base and a fragrance be held in an open/closed vessel at 80° C. ( 176° F.) for up to 4 hours. To demonstrate the ability of the present enrobed processes to reduce fragrance loss, two samples were set up as follows:

Control (Non Protected Perfume)

48 grams of Varisoft 136-100 was melted in a convection-draft oven at 80° C. ( 176° F.). 2 grams of PNF217FPN (Fragrance level=4%) was added to the Varisoft composition and held at 80° C. for 4 hours in an open beaker.

Enrobed Composition 40 grams of Varisoft 136-100 base was melted in a convection-draft oven at 80° C. ( 176° F.) and 10 grams of a protected fragrance matrix according to the present invention ( 20% PNF217FPN 4% fragrance level) from Example 1 was added to the base. The mixture was held at 80° C. for 4 hours in an open beaker.

Both samples were extracted and analyzed. The results are shown in Table 2.

TABLE 2

Fragrance Loss From Base After 4 Hours in an Open Vessel at 80° C.

| Control | | Enrobed Composition | |
|---|---|---|---|
| % Fragrance | % Loss | % Fragrance | % Loss |
| 2.2 | 45% | 2.9 | 27% |

As Table 2 indicates, when the enrobed composition of the present invention is added to the melted base and left for four hours, the amount of fragrance loss is reduced by about 50% as compared to the control.

The above-referenced experiment was repeated but in a closed vessel rather than an open beaker. The results are shown in Table 3 below:

TABLE 3

| Fragrance Loss From Base After 4 Hours in a Covered Vessel at 80° C. | | | |
|---|---|---|---|
| Control | | Enrobed Composition | |
| % Fragrance | % Loss | % Fragrance | % Loss |
| 2.92 | 27% | 3.32 | 17% |

As Table 3 indicates, even in a closed vessel the Enrobed composition of the present invention reduced the amount of fragrance loss by about 50% compared to the control.

Example 4

Effect of Prolonged Heating on Enrobed vs. Unprotected Compositions

A commercially available fragrance PNF217FPN (Givaudan Roure) was used to determine what effect prolonged heating would have on a conventionally prepared fabric conditioner base and a fabric conditioner base containing a protected fragrance matrix according to the present invention.

Control and enrobed samples as described in Example 3 were heated and maintained at 80° C. for 8 hours. Samples were taken every 2 hours, extracted and analyzed by GC-MS. The data obtained is set forth in Table 4 below:

TABLE 4

| Fragrance Level Summary | | | | | |
|---|---|---|---|---|---|
| | Time (Hours) | | | | |
| Sample | 0 hrs | 2 hrs | 4 hrs | 6 hrs | 8 hrs |
| Conventional | 3.6 | 3.3 | 3.2 | 3.1 | 2.9 |
| Enrobed (Protected) | 3.9 | 3.9 | 3.7 | 3.7 | 3.5 |

As Table 4 indicates, the protected fragrance matrix does not evaporate as much as the neat oil and affords protection from the heated environment.

Table 5 shows the amount of fragrance lost from the system. After 8 hours at 80° C., the enrobed fragrance matrix still contains twice as much fragrance as the conventional formulation.

TABLE 5

| Fragrance Loss Summary | | | | | |
|---|---|---|---|---|---|
| | Time (Hours) | | | | |
| Sample | 0 hrs | 2 hrs | 4 hrs | 6 hrs | 8 hrs |
| Conventional | 10% | 17.5% | 20% | 22.5% | 27% |
| Enrobed (Protected) | 2.5% | 2.5% | 7.5% | 7.5% | 12.5% |

As Table 5 demonstrates, the use of the protected fragrance matrix, according to the present invention, does protect the fragrance to the extent that even after prolonged heating losses are less than those experienced under conventional production conditions.

Example 5

Enrobed vs. Unprotected Compositions

The manufacture of fabric softener sheets requires that the melted fabric softener base and fragrance be held in an open/closed vessel at about 80° C. ( 176° F.) and continuously added to a coating pan which is also maintained at about 80° C. ( 176° F.). To demonstrate the ability of Enrobed compositions of the present invention to reduce fragrance loss, two samples were set up as follows:

Sample 1 (Control)

48 grams of Varisoft 136-100 base was melted in a convection-draft oven at 80° C. ( 176° F.). 2 grams of PNF217FPN (Fragrance level=4%) was immediately added to the base and fabric softener sheets prepared.

Sample 2 (Enrobed Composition)

40 grams of Varisoft 136-100 base was melted in a convection-draft oven at 80° C. ( 176° F.) and added to a coating pan. When the temperature was stable, 10 grams of the Enrobed composition of the present invention containing PNF217FPN ( 20% fragrance=4% fragrance level) from Example 1 was added to the base and fabric softener sheets were prepared.

Fabric softener sheets from both experiments were extracted and analyzed. The results are shown in Table 6.

TABLE 6

| Fragrance Loss From Fabric Softener Sheets With and Without Enrobement | | | |
|---|---|---|---|
| Control | | Enrobed | |
| % Fragrance | % Loss | % Fragrance | % Loss |
| 2.86 | 29% | 3.55 | 11.3% |

As Table 6 indicates, the enrobed composition of the present invention reduced the amount of fragrance loss by about 60% compared to the control.

Example 5

One of the highest levels of fragrance loss during the manufacture of fabric softener sheets occurs when the sheets are cooled. Adding fragrance near the end of the process or after coating should significantly reduce fragrance loss.

To test this hypothesis, a protected fragrance matrix according to the present invention was sprinkled uniformly onto the surface of warm sheets freshly coated with Varisoft fabric softener base. The sheets were then cooled, extracted, and analyzed.

Table 7 compares the fragrance loss of conventionally prepared sheets to sheets prepared using the Enrobed composition of Example 1 after coating.

TABLE 7

| Fragrance Loss From Fabric Softener Sheets With and Without Protected Fragrance Matrixes | | | |
|---|---|---|---|
| Normal Coating Process | | Enrobed Fragrance | |
| % Fragrance | % Loss | % Fragrance | % Loss |
| 2.4 | 40% | 3.88 | 3% |

As Table 7 indicates, adding the Enrobed composition (Enrobed Fragrance) from Example 1 to warm fabric softener base-coated sheets significantly reduces fragrance loss by about 90% compared to conventional coating processes.

Example 6

Comparison of Effect of Different Fixatives in Enrobed Composition

Three different samples were prepared as in Example 1 except that the following fixatives were substituted for the polyethylene glycol 4,000 recited therein: (a) polyethylene glycol with a molecular weight of 20,000 daltons; (b) Glycerox (a triglyceride mixture) with a molecular weight of about 2,000 daltons; and (c) mineral oil, with a molecular weight of approximately 400 daltons.

Dryer Sheet Preparation:

Immediate Application:

Varisoft 136-100 (Witco) was used as the fabric conditioner base. It was heated to 80° C. in a convection oven. For each of the three samples, 40 g of Varisoft were placed into a pre-heated beaker. 10 g of the Enrobed composition as prepared in Example 1 was added with mixing. 1.5 g of the molten mixture was evenly spread on a 1 g blank woven polyester dryer sheet.

4 Hour Heat/Hold Application:

Varisoft was heated to 80° C. in a convection oven. 40 g of the Varisoft was weighed into a pre-heated beaker and 10 g of the enrobed fragrance matrix was added, mixed and held at 80° C. for 4 hours and then applied onto a sheet using the same procedure as above.

The fragrance level of each sheet was determined by Soxhlet extraction followed by GC-MS analysis. The results are shown in Table 8 below.

TABLE 8

| Sample | Fragrance (%) | Loss (%) |
|---|---|---|
| PEG 20000 | 3.94 | 1.5 |
| Glycerox | 3.42 | 14.5 |
| Mineral Oil | 3.51 | 12.3 |
| Conventional-4 hour heat/hold | 3.18 | 21 |
| Mineral Oil-4 hour heat/hold | 3.08 | 23 |
| Conventional Dryer Sheet | 2.4 | 40 |

As the data in Table 8 indicate, each of the three fixatives used with the protected fragrance matrix of the present invention reduce fragrance loss compared to a conventionally prepared dryer sheet. The higher molecular weight (PEG 20,000) sample provides the best effect of the three fixatives tested exhibiting a percent fragrance loss of only 1.5%.

A similar fragrance protection was also evident in the 4-hour heat/hold samples as well. The immediate application of the protected fragrance matrix continues to be the best variant. However, even the heat/held dryer sheets showed a 53% improvement in fragrance loss when compared to the conventionally prepared product.

Example 7

Effect of Absorbents on Protected Fragrance Matrix

Enrobement or protection of the perfume in the fragrance matrix may be broken up into two parts: the fixative and the absorbent. In this example, the absorbent effects, particularly the replacement of clay and Zeolite absorbents with several other absorbents is shown. The fragrance absorption capacity of the dry blends was also tested and is presented below.

Alternative absorbents to Zeolite and clay were tested as follows; starch, methyl cellulose, sodium sulfate, sodium bicarbonate and sodium borate. Blends of these alternative absorbents were prepared at 50% with Zeolite, 75% with clay, and at 100% with no Zeolite or clay.

Results are listed in Tables 9–11. The sodium bicarbonate and sodium borate Blended 50/50 with Zeolite and 20% fragrance formed a pasty wet mass (sodium bicarbonate) and large moist clumps (sodium borate). Replacing the Zeolite with clay had the same results. These results indicate that sodium bicarbonate and sodium borate are not optimal absorbents.

The starch, methyl cellulose and sodium sulfate all performed well either blended with Zeolite or clay. They remained free flowing and easily absorbed up to 40% fragrance before showing any signs of clumping.

Thus, the data in Tables 9–11 indicate that several materials are suitable for use as absorbents in the present fragrance matrix either in place of or blended with Zeolite and clay. As Tables 9–11 also indicate, the absorbent blends have a capacity of up to about 40% fragrance while remaining free flowing and homogeneous.

Tables 9–11 also demonstrate that various carriers and fragrances may be used in the present fragrance matrix by balancing each component to produce a free-flowing powder that is easily handled and applied to e.g., fabric softener sheets. Thus, any combination of a fragrance and a suitable carrier that results in a free flowing composition that is easily handled and dosed is encompassed by the present invention.

TABLE 9

Absorbent Summary: 50/50 Sample/Zeolite Blend

| | Fragrance Amount | | Free Flowing Powder | |
|---|---|---|---|---|
| Sample | 20% | 30% | 20% | 30% |
| Starch | Good | No Good | Free Flowing | Wet Paste-NG |
| Methyl Cellulose | Good | Good | Free Flowing | Free Flowing |
| Sodium Sulfate | Good | No Good | Free Flowing | Wet Clumps |
| Sodium Bicarbonate | No Good | N/A | Wet Paste | N/A |
| Sodium Borate | No Good | N/A | Wet Clumps | N/A |

TABLE 10

Absorbent Summary: 75/25 Sample/Clay Blend

| | Fragrance Amount | | Free Flowing Powder | |
|---|---|---|---|---|
| Sample | 20% | 30% | 20% | 30% |
| Starch | Good | Good | Free Flowing | Free Flowing |
| Methyl Cellulose | Good | Good | Free Flowing | Free Flowing |
| Sodium Sulfate | Good | Good | Free Flowing | Free Flowing |
| Sodium Bicarbonate | No Good | N/A | Wet Paste | N/A |
| Sodium Borate | No Good | N/A | Wet Clumps | N/A |

TABLE 11

Absorbent Summary: 100% Sample

| | Fragrance Amount | | Free Flowing Powder | |
|---|---|---|---|---|
| Sample | 20% | 30% | 20% | 30% |
| Starch | Good | No Good | Free Flowing | Wet Paste- NG |
| Methyl Cellulose | Good | No Good | Free Flowing | Free Flowing |
| Sodium Sulfate | Good | No Good | Free Flowing | Wet Clumps |
| Sodium Bicarbonate | No Good | N/A | Wet Paste | N/A |
| Sodium Borate | No Good | N/A | Wet Clumps | N/A |

Example 8

Comparison of the Fragrance Retention of Conventional and Enrobed Dryer Sheets

Fabric softener sheets were prepared by adding the appropriate amounts of protected fragrance matrix, as set forth in Example 1, on to a blank polyester sheet dosed with the applicable amount of active as set forth in Example 1. This process simulates post dosing and was prepared at a fragrance level of 4%, and compared to a conventionally prepared sheet.

Headspace GC-MS measurements were made from conventionally prepared fabric softener sheets, from fabric softener sheets prepared according to the present invention, and from towels that had been washed, then dried, with the respective fabric softener sheets. The results set forth in Table 12 indicate that the sheets containing the protected or enrobed fragrance, i.e., the fabric softener sheets made according to the present invention, retain far more fragrance and deposit much more fragrance on to towels in the dryer compared to commercially available alternatives.

Moreover, in an olfactive assessment the 4% protected fragrance matrix-containing dryer sheets were unanimously ranked higher for fragrance strength and hedonics.

TABLE 12

Headspace Comparison: Enrobed Dryer Sheets

| Sample | Fragrance: Ng/Liter |
|---|---|
| Conventional Market Sheet | 11,000 |
| 4.0% Enrobed Sheet | 28,000 |
| Dried Towel Conventional Sheet | 41 |
| Dried Towel 4.0% Enrobed | 192 |

Thus, the data in Table 12 indicate that protecting the perfume component of the fragrance matrix by enrobement does provide protection to the fragrance during high temperature preparation of dryer sheets.

The invention being thus described, it will be obvious that the same may be varied in many ways. Such variations are not to be regarded as a departure from the spirit and scope of the invention and all such modifications are intended to be included within the scope of the following claims.

We claim:

1. A process for reducing fragrance loss in a substrate comprising preparing a protected fragrance matrix comprising a perfume, a solid absorbent, and a fixative, and combining the fragrance matrix with a fabric conditioner base and the substrate to impregnate the substrate with the fragrance matrix and fabric conditioner base, wherein the perfume to solid absorbent ratio is from about 1:20 to about 2:5.

2. A process according to claim 1 wherein the fragrance matrix is combined with the fabric conditioner base to form a mixture, and immediately applying the mixture to the substrate.

3. A process according to claim 1 wherein the fabric conditioner base is combined with the substrate to form a substrate-fabric conditioner base composition and then the fragrance matrix is combined with the substrate-fabric conditioner base composition.

4. A process according to claim 1 further comprising dispersing the fabric conditioner base and the fragrance matrix throughout the substrate to a uniform thickness of about 0.1 to about 2.0 mm.

5. A process according to claim 1 wherein the solid absorbent is selected from the group consisting of clays, silicas, zeolites, metal salts, celluloses, starches, carbonates, borates, sulfates, water-soluble polymers, borax, and mixtures thereof.

6. A process according to claim 1 wherein the solid absorbent is selected from the group consisting of zeolites, clays, methyl celluloses, sodium sulfates, starches, bicarbonates and mixtures thereof.

7. A process according to claim 1 wherein the fixative is selected from the group consisting of polyethylene glycol, triglycerides, mineral oil and mixtures thereof.

8. A process according to claim 7 wherein the polyethylene glycol has a molecular weight of from about 400 to 20,000 daltons.

9. A process according to claims 7 wherein the polyethylene glycol has a molecular weight from about 2,000 to 10,000 daltons.

10. A process according to claim 1 wherein the fabric conditioner base comprises a fabric softener selected from the group consisting of cationic softeners, zwitterionic softeners, non-ionic softeners and mixtures thereof.

11. A process according to claim 10 wherein the fabric conditioner base further comprises a component selected from the group consisting of an antistatic agent an anti-dye transfer agent, a soil release agent and mixtures thereof.

12. A process according to claim 1 wherein the fragrance mixture comprises additional fragrance components.

13. A process according to claim 1 wherein the fragrance matrix comprises perfume in an amount of from about 10% to about 50%.

14. A process according to claim 1 wherein the fragrance matrix comprises perfume in an amount of from about 20% to about 40%.

15. A process according to claim 1 wherein the substrate is a synthetic or natural material.

16. A process according to claim 15 wherein the substrate is selected from the group consisting of polyester, regenerated cellulose, cellulose and mixtures thereof.

17. A process according to claim 1 wherein the substrate is a sheet.

18. A process according to claim 1 wherein the perfume to solid absorbent ratio is from about 1:5.

19. A substrate made from the process of claim 1.

20. A fabric treated with a substrate made by the process of claim 1.

21. A substrate impregnated with a fragrance matrix having prolonged organoleptic activity prepared by the process comprising:

(a) forming a protected fragrance matrix comprising a perfume, a fixative and a solid absorbent;

(b) applying the fragrance matrix and a fabric conditioner base to the substrate, wherein the fragrance matrix is mixed wit the fabric conditioner base immediately prior to application of the mixture to the substrate or the fragrance matrix is applied to the fabric conditioner base immediately after the fabric conditioner base is applied to the substrate, (c) wherein the perfume to solid absorbent ratio is from about 1:20 to about 2:5.

22. The substrate of claim 21 wherein the perfume to solid absorbent ratio is from about 1:5.

23. The substrate of claim 21 wherein the fixative is a low melting point, high molecular weight composition.

24. The substrate of claim 21 wherein the fixative is selected from the group consisting of polyethylene glycol, triglycerides, mineral oil and mixtures thereof.

25. A process according to claim 1 wherein the fixative is a low melting point, high molecular weight composition.

* * * * *